(12) United States Patent
Paoletti

(10) Patent No.: US 8,730,332 B2
(45) Date of Patent: May 20, 2014

(54) SYSTEMS AND METHODS FOR ERGONOMIC MEASUREMENT

(75) Inventor: Tomaso Paoletti, San Mateo, CA (US)

(73) Assignee: DigitalOptics Corporation, San Jose, CA (US)

(*) Notice: Subject to any disclaimer, the term of this patent is extended or adjusted under 35 U.S.C. 154(b) by 388 days.

(21) Appl. No.: 12/893,674

(22) Filed: Sep. 29, 2010

(65) Prior Publication Data
US 2012/0075483 A1 Mar. 29, 2012

(51) Int. Cl.
H04N 5/225 (2006.01)

(52) U.S. Cl.
USPC ....................................... 348/207.1

(58) Field of Classification Search
None
See application file for complete search history.

(56) References Cited

U.S. PATENT DOCUMENTS

| | | | |
|---|---|---|---|
| 5,164,717 A | 11/1992 | Wells et al. | |
| 5,661,539 A | 8/1997 | Sheedy | |
| 6,076,928 A | 6/2000 | Fateh et al. | |
| 6,275,614 B1 | 8/2001 | Krishnamurthy et al. | |
| 6,448,769 B1 | 9/2002 | Rosenfeld et al. | |
| 6,937,745 B2 | 8/2005 | Toyama | |
| 7,079,674 B2 | 7/2006 | Paragios et al. | |
| 7,165,715 B2 | 1/2007 | Elgie et al. | |
| 7,188,772 B2 | 3/2007 | Elgie et al. | |
| 7,315,249 B2* | 1/2008 | Littell .......................... | 340/573.7 |
| 7,565,030 B2 | 7/2009 | Steinberg et al. | |
| 7,583,253 B2 | 9/2009 | Jeng et al. | |
| 7,626,569 B2 | 12/2009 | Lanier | |
| 7,826,642 B2 | 11/2010 | Cherkassky et al. | |
| 8,024,202 B2* | 9/2011 | Carroll et al. ..................... | 705/3 |
| 8,488,023 B2 | 7/2013 | Bacivarov et al. | |
| 2002/0015423 A1 | 2/2002 | Rakib et al. | |
| 2002/0102024 A1 | 8/2002 | Jones et al. | |
| 2002/0105482 A1 | 8/2002 | Lemelson et al. | |
| 2002/0149603 A1 | 10/2002 | Frisken et al. | |
| 2004/0148577 A1 | 7/2004 | Xu et al. | |
| 2006/0017739 A1 | 1/2006 | Fang et al. | |
| 2006/0071135 A1 | 4/2006 | Trovato | |
| 2007/0110305 A1 | 5/2007 | Corcoran et al. | |
| 2007/0216709 A1 | 9/2007 | Kojima et al. | |
| 2007/0296556 A1 | 12/2007 | Wang et al. | |

(Continued)

FOREIGN PATENT DOCUMENTS

| | | |
|---|---|---|
| WO | WO 2008/107002 A1 | 9/2008 |
| WO | 2010/030985 A1 | 3/2010 |
| WO | WO 2010/060211 A1 | 6/2010 |
| WO | 2012/050878 A1 | 4/2012 |

OTHER PUBLICATIONS

U.S. Appl. No. 12/790,594.
U.S. Appl. No. 12/825,280.

(Continued)

Primary Examiner — Luong T Nguyen
(74) Attorney, Agent, or Firm — Hickman Palermo Truong Becker Bingham Wong LLP

(57) ABSTRACT

Systems and methods for ergonomic measurement are disclosed. For example, in one embodiment a method for ergonomic measurement includes: receiving a first signal from an image sensor, the first signal comprising data associated with a user's orientation with respect to the image sensor. A second signal is received from a orientation sensor, the second signal comprising data associated with the image sensor's orientation with respect to gravity. An ergonomic measurement of the user is determined based at least in part on the first and second signals. Another embodiment includes a computer-readable medium comprising processor-executable code for executing such a method.

22 Claims, 5 Drawing Sheets

(56) References Cited

U.S. PATENT DOCUMENTS

| | | | |
|---|---|---|---|
| 2008/0013798 | A1 | 1/2008 | Ionita et al. |
| 2008/0175481 | A1 | 7/2008 | Petrescu et al. |
| 2008/0219517 | A1 | 9/2008 | Blonk et al. |
| 2008/0225125 | A1 | 9/2008 | Silverstein et al. |
| 2008/0259325 | A1 | 10/2008 | Engelbart et al. |
| 2009/0003661 | A1 | 1/2009 | Ionita et al. |
| 2009/0037137 | A1 | 2/2009 | Takeda et al. |
| 2009/0133051 | A1 | 5/2009 | Hildreth |
| 2009/0138805 | A1 | 5/2009 | Hildreth |
| 2009/0179998 | A1 | 7/2009 | Steinberg et al. |
| 2009/0185753 | A1 | 7/2009 | Albu et al. |
| 2009/0190803 | A1 | 7/2009 | Neghina et al. |
| 2009/0324024 | A1 | 12/2009 | Worthington |
| 2009/0326552 | A1 | 12/2009 | Diolaiti |
| 2011/0037639 | A1 | 2/2011 | Duran Toro et al. |
| 2011/0080290 | A1* | 4/2011 | Baxi et al. .................. 340/573.1 |
| 2011/0275939 | A1* | 11/2011 | Walsh et al. .................. 600/473 |

OTHER PUBLICATIONS

Yang, M. et al., "Detecting Faces in Images: A Survey," 2002, IEEE Transactions on Pattern Analysis and Machine Intelligence, vol. 24, 21 pages.

PCT Notification of Transmittal of the International Search Report and the Written Opinion of the International Searching Authority, or the Declaration, for PCT Application No. PCT/US2011/053643, report dated Mar. 16, 2012, 10 pages.

Matsumoto Y, Ido J, Takemura K, Koeda M, Ogasawara T: "Portable facial information measurement system and its application to human modeling and human interfaces", Automatic Face and Gesture Recognition, 2004. Proceedings. Sixth IEEE International Conference on, May 17, 2004, IEEE, Piscataway, NJ, USA, pp. 475-480, XP010949478, ISBN: 978-0-7695-2122-0.

Straker L M, Coleman J, Skoss R, Maslen B A, Burgess-Limerick R, Pollock C M: "A comparison of posture and muscle activity during tablet computer, desktop computer and paper use by young children", Ergonomics, Taylor and Francis, London, GB, vol. 51, No. 4, Apr. 2008, pp. 540-555, XP002670129, ISSN: 0014-0139, DO1:10.1080/00140130701711000.

PCT Notification Concerning Transmittal of International Preliminary Report on Patentability (Chapter I of the Patent Cooperation Treaty), International Preliminary Report on Patentability, Chapter I of the Patent Cooperation Treaty, for PCT Application No. PCT/US2011/053643, report dated Apr. 2, 2013, 8 pages.

Non-Final Rejection, dated Apr. 10, 2013, for U.S. Appl. No. 13/082,568, filed Apr. 8, 2011.

* cited by examiner

SYSTEMS AND METHODS FOR ERGONOMIC MEASUREMENT

FIELD OF THE INVENTION

The present invention generally relates to ergonomics and more particularly to systems and methods for ergonomic measurement.

BACKGROUND

Many users of electronic devices spend long periods of time using their devices. Some of these users may, at times, fail to maintain a body or head orientation, or hold a device in a manner that minimizes or eliminates the likelihood of fatigue, strain, or other injury. New systems and methods for performing ergonomic measurement are needed to help users of portable, adjustable, and mobile communications, computing, productivity and other electronic devices maintain proper posture and minimize the likelihood of injury or other damage to their bodies.

SUMMARY

Embodiments of the present invention provide systems and methods for ergonomic measurement. For example, in one embodiment a method for ergonomic measurement comprises: receiving a first signal from an image sensor, the first signal comprising data associated with a user's orientation with respect to the image sensor. A second signal is received from an orientation sensor, the second signal comprising data associated with the image sensor's orientation with respect to gravity. An ergonomic measurement of the user is determined based at least in part on the first and second signals. Another embodiment comprises a computer-readable medium comprising processor-executable code for executing such a method.

Another embodiment comprises a system for performing ergonomic measurements comprising an image sensor configured to transmit a first signal comprising data associated with a user's orientation with respect to the image sensor. The system also includes an orientation sensor, an output, and a processor in communication with the image sensor, the orientation sensor, and the output, such as a display device. The orientation sensor is configured to transmit a second signal comprising data associated with the image sensor's orientation with respect to gravity. In this embodiment the processor is configured to: determine an ergonomic measurement of the user based at least in part on the first and second signals and transmit an ergonomic signal based at least in part on the ergonomic measurement. The output is configured to provide a message to the user based at least in part on the ergonomic signal.

These illustrative embodiments are mentioned not to limit or define the invention, but rather to provide examples to aid understanding thereof. Illustrative embodiments are discussed in the Detailed Description, which provides further description of the invention. Advantages offered by various embodiments of this invention may be further understood by examining this specification.

BRIEF DESCRIPTION OF THE DRAWINGS

These and other features, aspects, and advantages of the present invention are better understood when the following Detailed Description is read with reference to the accompanying drawings, wherein.

DETAILED DESCRIPTION

Figure 1:
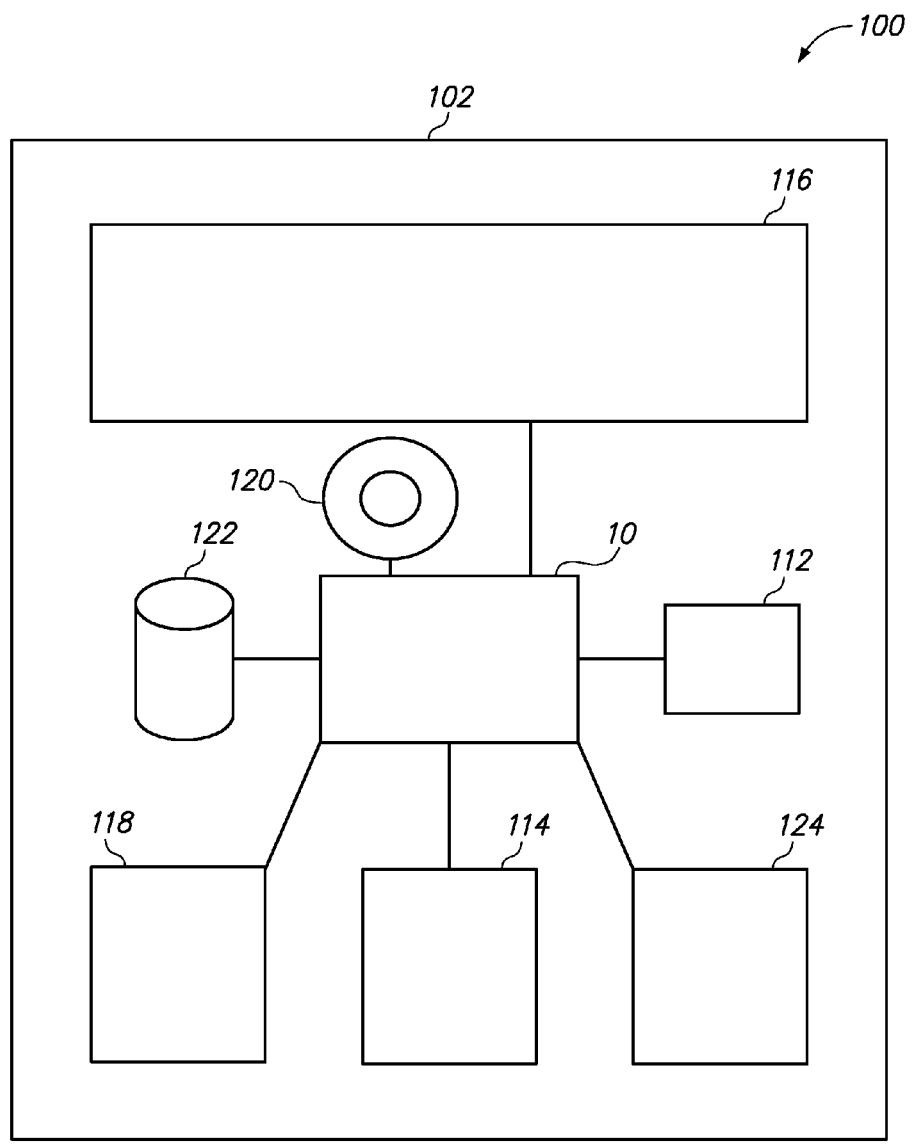
FIG. 1 is a block diagram of a system for ergonomic measurement according to one embodiment of the present invention.

Embodiments of the present invention provide systems and methods for ergonomic measurement.

Illustrative Embodiment of Ergonomic Measurement

One illustrative embodiment of the present invention comprises a system, such as a laptop computer programmed with appropriate computer code, which can be used by a user to perform various functions while in multiple different surroundings and user and device positions.

In the illustrative embodiment, the system includes an image sensor, such as a micro-optic lens device available from DigitalOptics™, which can be built into the bezel of a laptop computer's display screen. The image sensor is configured to collect and transmit a signal comprising data associated with the device user's orientation with respect to the image sensor. In other embodiments, different devices or and image sensors may be utilized, for example a desktop computer with an adjustable USB-connected camera, or a device similar to an Apple® iPhone™ or iPad™ mobile device having an image sensor built into the housing of the device.

In addition to the image sensor, the illustrative embodiment comprises a power source, a display, a speaker, an orientation sensor, a memory for storing computer code, and a processor that is in communication with each of the other elements.

In the illustrative embodiment, the display is configured to display a graphical user interface. The display can be used to provide visual messages to the user about his or her ergonomic measurements. In some embodiments the display may also function as a user input device, for example, using touch-screen technologies. The speaker can be used to provide audible messages to the user, either in coordination with, or instead of, providing messages via the display.

In the illustrative embodiment the orientation sensor is able to measure and provide data associated with the image sensor's orientation with respect to gravity, the gravitational force exerted by the Earth. The information measured by the orientation sensor can be used to interpret, correct, or adjust the data captured by the image sensor, so that one or more aspects of the user's orientation with respect to the gravitational force exerted by the Earth can be measured to determine whether or not he or she is maintaining a posture or position likely to minimize injury, strain, or fatigue.

The memory contains program code for instructing the processor how and when to collect signals from the image sensor and the orientation sensor and transform the data contained in the signals by performing calculations to determine an ergonomic measurement based at least in part upon those signals, and transmit an ergonomic signal based at least on part on the ergonomic measurement to be outputted in a message understandable by the user, for example, via a pop-up warning text box visible on the display, or via an audible signal output by the speaker.

To perform the ergonomic measurement, the processor may, for example, use program code stored in the memory to perform a facial recognition algorithm to determine the orientation of the user's face with respect to the image sensor, and then use data from the orientation sensor regarding the image sensor's orientation with respect to the gravitational force exerted by the Earth to determine an ergonomic measurement of the user, for example, the pitch and/or roll angle of the user's head with respect to the gravitational force exerted by the Earth.

This illustrative example is given to introduce the reader to the general subject matter discussed herein. The invention is not limited to this example. The following sections describe various additional non-limiting embodiments and examples of systems and methods for ergonomic measurement.

Illustrated System for Ergonomic Measurement

Referring now to the drawings in which like numerals indicate like elements throughout the several figures, FIG. 1 is a block diagram of a system for ergonomic measurement according to one embodiment of the present invention. As shown in FIG. 1, the system 100 comprises a device 102, such as a mobile phone, portable digital assistant (PDA), portable gaming device, laptop computer, netbook computer, or tablet computer. The device 102 comprises a processor 110 in communication with a network interface 112, an image sensor 114, a display 116, an orientation sensor 118, a speaker 120, a memory 122, and a power supply 124. The processor 110 is configured to generate a graphical user interface, which is shown on display 116, and to generate signals to be output as audible messages via the speaker 120.

The processor 110 is configured to execute computer-executable program instructions stored in memory 122. For example, processor 110 may execute one or more computer programs for recognizing the orientation of at least part of the face of a user. Processor 110 may comprise a microprocessor, a digital signal processor (DSP), an application-specific integrated circuit (ASIC), one or more field programmable gate arrays (FPGAs), or state machines. Processor 110 may further comprise a programmable electronic device such as a programmable logic controller (PLC), a programmable interrupt controller (PIC), a programmable logic device (PLD), a programmable read-only memory (PROM), an electronically programmable read-only memory (EPROM or EEPROM), or other similar devices.

Memory 122 comprises a computer-readable medium that stores instructions, which when executed by processor 110, causes processor 110 to perform various steps, such as those described herein. Embodiments of computer-readable media may comprise, but are not limited to, electronic, optical, magnetic, or other storage or transmission devices capable of providing processor 110 with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. In addition, various other devices may provide computer-readable media such as a router, private or public network, or other transmission devices. The processor 110 and the processing described may be in one or more structures, and may be dispersed throughout one or more structures.

The processor 110 is in communication with the network interface 112. The network interface 112 may comprise one or more methods of mobile communication, such as infrared, radio, Wi-Fi, or cellular network communication. In other variations, the network interface 112 comprises a wired network interface, such as Ethernet. The device 102 can be configured to exchange messages with other devices (not shown) over networks such as a cellular network and/or the Internet. Embodiments of messages exchanged between devices may comprise data messages, voice messages, text messages, or other forms of digital messages.

The processor 110 is also in communication with one or more image sensors 114. The image sensor 114 may comprise a miniaturized camera device, a micro-optic lens device, micro-mirror MEMS device, or some other type of suitable device known in the art that can be configured to capture information associated with at least a visible portion of a user of the device 102, such as the user's face. In some embodiments, the processor is in communication with a single image sensor 114, in other embodiments, the processor is in communication with a plurality of image sensors, for example, a MEMS camera on the front and back of a device's case. The image sensor 114 is configured to detect at least a visible portion of a user of the device 102, and based on the detected portion, transmit signals to processor 110 comprising data associated with a user's orientation with respect to the image sensor.

In the embodiment shown in FIG. 1, the processor 110 is also in communication with a display 116. For example, the display 116 can be a thin-film transistor liquid crystal display, or an LED display. The processor 110 can be configured to generate a graphical representation of a user interface to be shown on display 116. In some embodiments, the display 116 may comprise a manipulandum, such as a touch-sensitive interface. In such an embodiment, the touch-sensitive interface may comprise a touch-screen mounted overtop of display 116.

As shown in FIG. 1, processor 110 is also in communication with one or more orientation sensors 118. Orientation sensor 118 is configured to capture information associated with the orientation sensor's 118 orientation with respect to the gravitational force exerted by the Earth in one or more axes, and to transmit a signal comprising the captured data. Processor 110 is configured to receive the signal comprising data associated with the image sensor's orientation with respect to the gravitational force exerted by the Earth from the orientation sensor 118. Orientation sensor 118 may be, for example, an accelerometer, such as a micro-electro-mechanical system (MEMS) accelerometer available from Siimpel Corporation. In some embodiments the orientation sensor can include multiple accelerometers, each configured to measure acceleration in one or more different axes, or can comprise a different type of sensor, such as a MEMS gyroscope or an inertial measurement unit (IMU).

As shown in FIG. 1, processor 110 is also in communication with speaker 120. Speaker 120 is configured to receive audio signals from processor 110 and output them to the user. In some embodiments, the audio signals may be associated with the ergonomic signal output by the processor 110, or the image output by display 116. In other embodiments, the audio signal may not correspond to the ergonomic signal or the image.

The power supply 124 can be a rechargeable battery, such as a lithium-ion or NiMH battery, or another suitable type of power supply, for example a suitably-sized AC to DC converter plugged into a household 120 electrical outlet.

Facial recognition algorithms can be performed by the processor 110 to ascertain the orientation of a device user with respect to the image sensor 114. For example, Yang et al., IEEE Transactions on Pattern Analysis and Machine Intelligence, January 2002, Vol. 24, No. 1, pages 34-58, which is incorporated by reference, provides a review of facial detection techniques. Illustrative types of facial detection techniques can be divided into four main categories: (i) knowledge-based methods; (ii) feature-invariant approaches, including the identification of facial features, texture and skin color; (iii) template matching methods, both fixed and deformable and (iv) appearance based methods, including eigenface techniques, statistical distribution based methods and neural network approaches.

One fast-face detection algorithm is disclosed in published patent application number US 2002/0102024 (hereinafter "Viola-Jones"), which is hereby incorporated in full by reference. One method described in Viola-Jones comprises deriving an integral image from an acquired image, which is usually an image frame in a video stream. Each element of the integral image is calculated as the sum of intensities of all points above and to the left of the point in the image. The total intensity of any sub-window in an image can then be derived by subtracting the integral image value for the top left point of the sub-window from the integral image value for the bottom right point of the sub-window. Also, intensities for adjacent sub-windows can be efficiently compared using particular combinations of integral image values from points of the sub-windows.

In a method described in Viola-Jones, a chain (cascade) of 32 classifiers based on rectangular (and increasingly refined) Haar features are used with the integral image by applying the classifiers to a sub-window within the integral image. For a complete analysis of an acquired image, this sub-window is shifted incrementally across the integral image until the entire image has been covered.

In addition to moving the sub-window across the entire integral image, the sub window in Viola-Jones is also scaled up/down to cover the possible range of face sizes. In Viola-Jones, a scaling factor of 1.25 is used and, typically, a range of about 10-12 different scales are used to cover the possible face sizes in an XVGA size image.

The resolution of the integral image is determined by the smallest sized classifier sub-window, i.e. the smallest size face to be detected, as larger sized sub-windows can use intermediate points within the integral image for their calculations.

A number of variants of an algorithm taught in Viola-Jones are known in the literature. These generally employ rectangular, Haar feature classifiers and use the integral image techniques of Viola-Jones.

Partial face detection techniques may also be advantageously utilized in certain embodiments, e.g., according to techniques described in U.S. patent application Ser. No. 12/790,594 and/or Ser. No. 12/825,280, both of which are hereby incorporated by reference.

A broad range of techniques may be employed in image manipulation and/or image enhancement with emphasis on the detection of faces in accordance with certain embodiments, as set forth for example at U.S. Pat. No. 7,565,030 and US published applications nos. 2009/0179998, 2007/0110305, and PCT publication WO2008/107002, which are assigned to the same assignee and hereby incorporated by reference. Such techniques may involve automatic, semi-automatic and/or manual operations, and are applicable to several fields of application. For example, rather than only applying luminance-based approaches, advanced color modeling may be employed, e.g., as set forth at US published applications nos. 2008/0013798 and 2008/0175481, and U.S. Pat. No. 6,275,614, which are hereby incorporated by reference.

Face detection can be successfully applied even in conditions of less than optimum facial pose and/or under a directional lighting condition in accordance with certain advantageous embodiments as set forth at US published applications nos. 2008/0219517, 2009/0185753, 2009/0190803 and 2009/0003661, which are assigned to the same assignee and hereby incorporated by reference.

Figure 2:
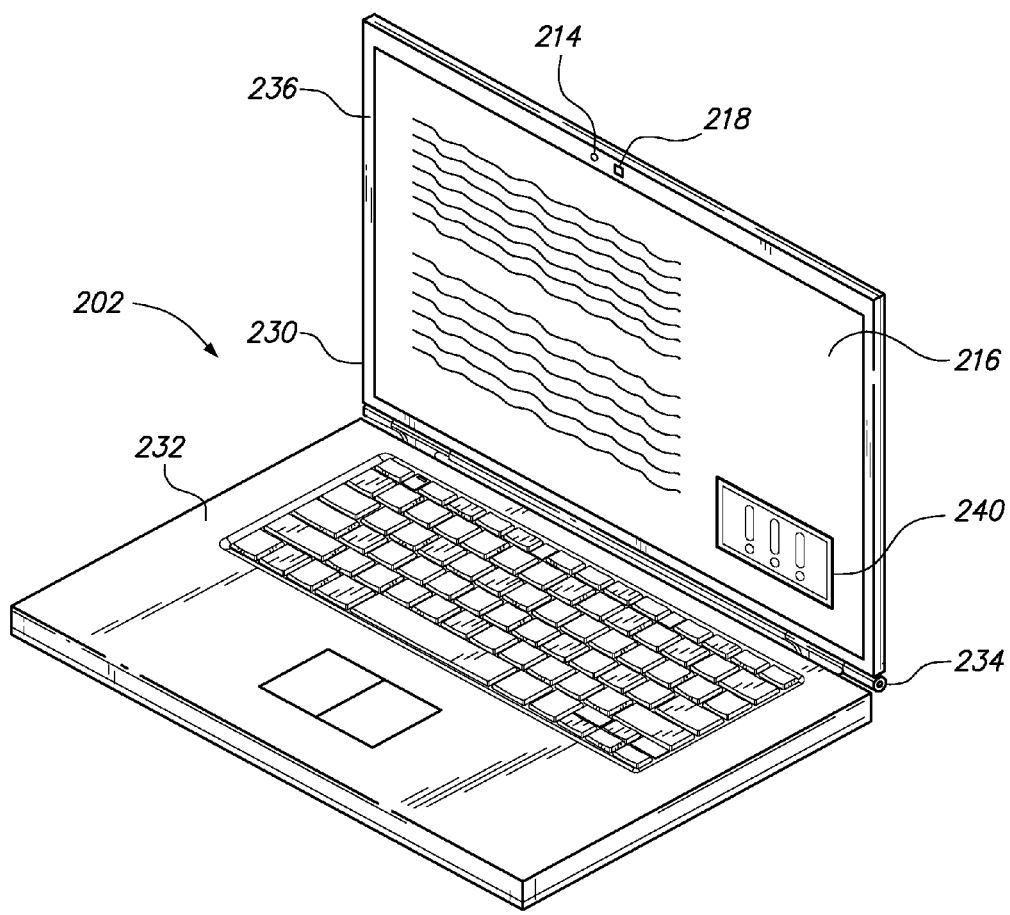
FIG. 2 is an illustrative embodiment of a system for ergonomic measurement according to one embodiment of the present invention.

FIG. 2 is an illustrative embodiment of a system for ergonomic measurement according to one embodiment of the present invention. FIG. 2 comprises a device 202. The device 202 is configured to allow a user to access applications and content stored both locally and through communications networks, such as a cellular network or the Internet. The device 202 may comprise a wireless network interface and/or a wired network interface (not shown in FIG. 2). Although the device 202 is illustrated as a laptop computer device in FIG. 2, other embodiments may comprise different devices, such as tablet computers, video game systems, smart phones, PDAs, and/or personal computers.

As shown in FIG. 2, the device 202 comprises an upper housing portion 230, a lower housing portion 232, a hinge 234 movably connecting the upper housing portion 230 to the lower housing portion 232, and a display 216 in the upper housing portion 230 surrounded by a bezel 236. In some embodiments, display 216 may comprise an LCD display. In other embodiments, display 216 may comprise a plasma display, or other type of display known in the art.

Referring still to FIG. 2, the device 202 further comprises an image sensor 214 mounted in the bezel 236 surrounding the display 216. In the embodiment shown in FIG. 2, the image sensor 214 comprises a miniature camera. Image sensor 214 is configured to detect at least a visible portion of a user, such as his or her face, and transmit signals corresponding to data associated with the user's orientation with respect to the image sensor 214 to a processor within the device 202.

The device 202 further comprises an orientation sensor 218 embedded in the bezel 236 surrounding the display 216 in a position such that it is configured to be able to provide data associated with the image sensor's 214 orientation with respect to the gravitational force exerted by the Earth. For example, the orientation sensor 218 may be positioned in close proximity to the image sensor 214. As shown in FIG. 2, the upper housing portion 230 can be adjusted with respect to the lower housing portion 232 with adjustability provided by the hinge 234 therebetween. For example, a user may adjust the angle of the upper housing portion 230 with respect to the lower housing portion 232 to meet his or her usage requirements or preferences, for example to account for a user's height, reduce glare on the display 216 caused by overhead lighting, or to account for a situation where the lower housing portion 232 is resting on a non-level surface. As the upper housing portion 230 is adjusted, the angle between the user and the image sensor 214 changes.

In the embodiment shown in FIG. 2, the orientation sensor 218 is mounted within the bezel 236 adjacent the image sensor 214 in order to provide an indication of the image sensor 214 with respect to the gravitational force exerted by the Earth. As such, an ergonomic measurement of the user (for example the orientation of the user's head, neck, or shoulders) with respect to the gravitational force exerted by the Earth can be determined be using data obtained from the image sensor 214 and the orientation sensor 218.

Still referring to FIG. 2, display 216 is configured to receive display signals from the processor within the device 202 and output them to the user. In some embodiments, the display signals may comprise a graphical user interface, which is displayed to the user via display 216. For example, one type of display signal is an ergonomic signal configured to provide information based at least in part on an ergonomic measurement determined by a processor within the device 202 using signals from the image sensor 214 and the orientation sensor 218. In the embodiment shown in FIG. 2, display 216 is displaying a user application, such as a word-processing application, to the user, along with a pop-up message box 240 displaying a message to the user regarding his or her posture based on an ergonomic signal transmitted by the processor to the display 216.

Figure 3:
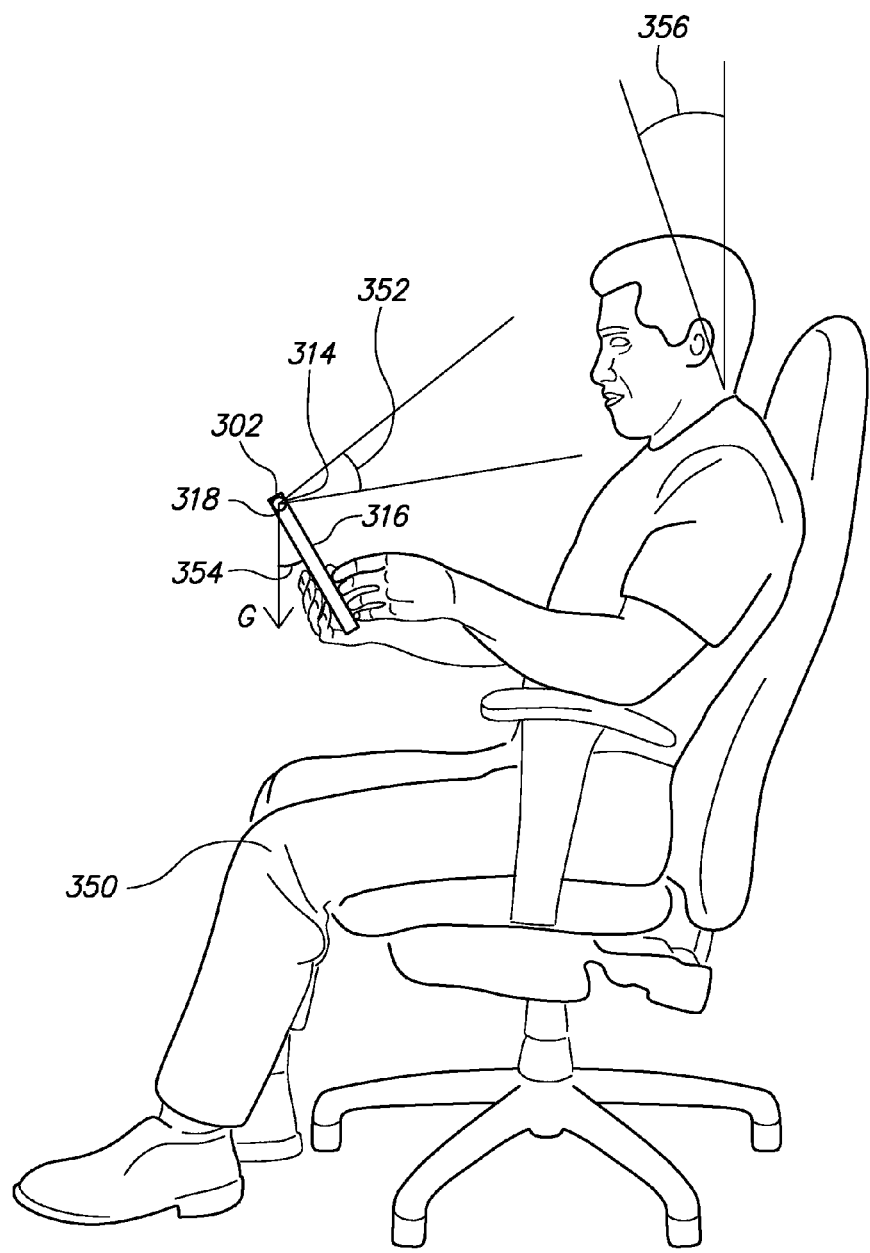
FIG. 3 is an illustration of a user using a device configured to perform an ergonomic measurement according to one embodiment of the present invention.

FIG. 3 is an illustration of a user 350 using a device 302 configured for ergonomic measurement according to one embodiment of the present invention. FIG. 3 shows device 302, which in the embodiment shown in FIG. 3 comprises a tablet computer. The device 302 comprises a display 316. Mounted within the device 302 are an image sensor 314, and an orientation sensor 318. The display 316 shown in FIG. 3 is a touch-screen display, and thus allows for the user 350 to provide input to the device 302 in addition to functioning as an output configured to provide messages to the user 350.

In the embodiment shown in FIG. 3, according to a periodic schedule contained in program code stored in a memory within the device 302 (not shown), the processor in the device 302 (not shown) obtains a signal from the image sensor 314 comprising data associated with one or more aspects of the user's 350 orientation with respect to the image sensor 314. For example, the signal may contain data associated with one or more of the orientation of the user's head, neck, or shoulders with respect to the image sensor 314.

For example, as shown in FIG. 3, the image sensor 314 has a field of view 352 configured to capture data that can be used with a facial recognition algorithm, such as described above for example, to determine an uncorrected pitch angle of the user 350 based at least in part on the distance between the top of the user's 350 head and his or her shoulders.

At the same time the processor in the device 302 obtains a signal from the orientation sensor 318 comprising data associated with the image sensor's 314 orientation with respect to the gravitational force exerted by the Earth, which can be used to determine the angle 354 between the image sensor's 314 orientation and gravity, the vertical gravitational force exerted by the Earth.

Using the signals obtained from the image sensor 314 and orientation sensor 318, the processor of the device 302 determines an ergonomic measurement of the user 350, which can be, for example, the pitch angle 356 of the user's 350 head with respect to the vertical gravity force exerted by the Earth. For example, pitch angle 356 may be determined by subtracting the angle 354 from the uncorrected pitch angle measured using a pose estimation algorithm using data signals provided by the image sensor 314.

In the embodiment shown in FIG. 3, the processor within the device 302 is configured to compare the ergonomic measurement of the user's 350 head pitch angle 356 to data in a signal comprising a predetermined ergonomic quality metric, such as a suggested range of acceptable head pitch angles provided by a guideline or standard. For example, ISO 9241-5, Ergonomic Requirements for Office Work with Visual Display Terminals (VDTs)—Part 5: Workstation Layout and Postural Requirements provides acceptable limits for a user's head position.

Based on such a comparison, the processor in device 302 can determine the ergonomic quality of one or more aspects of the user's 350 current orientation with respect to the gravitational force exerted by the Earth. Then, based on the determined ergonomic quality of the user 350, the processor of the device 302 transmits an ergonomic signal to the display 316, which can provide a message to the user 350 about his or her posture.

In some embodiments, the ergonomic quality metrics are defined by the user 350 and stored by the processor. In other embodiments, the ergonomic quality metrics come preloaded on the device 302 as default settings, for example, to reflect known ranges of acceptable and unacceptable values based on studies in the field of ergonomics. In still other embodiments, the processor may download the ergonomic quality metrics via a network interface, either in real-time or at predetermined or user-selected intervals.

In some embodiments, the processor may store the ergonomic quality metrics in a local data store on the device 302. In other embodiments, the processor may store the ergonomic quality metrics on an external data store accessed via a network interface. A user 350 may define ergonomic quality metrics based on his or her preferences. In some embodiments, the menu may allow the user 350 to assign ergonomic quality metrics based on a variety of factors associated with the device 302 usage orientations he or she regularly assumes. For example, in one embodiment, the user 350 may define a ergonomic quality metric associated with using the device 302 while seated but not using a desk (as shown in FIG. 3), as well as ergonomic quality metrics for using the device 302 while it is placed on a counter while the user 350 is standing or seated at a barstool, while the user 350 is holding the device 302 while standing, and while the user 350 is seated at a desk and the device 302 is either flat on the desk or oriented at angle, for example while placed in a docking station or an easel. In some embodiments, these quality metrics may be simple, for example, categorizing device usage orientations as ergonomic or non-ergonomic. In another embodiment, these quality metrics may be more complex, for example assigning levels of importance to various aspects of the user's 350 posture.

In some embodiments, the user 350 of the device 302 may further define other ergonomic quality metrics. For example, the user 350 may enter a menu that allows the user 350 to define ergonomic quality metrics associated with his or her known bad habits. In another embodiment, the graphical user 350 interface may display a menu that allows the user 350 to define parameters that are associated with the ergonomic quality of his or her relationship in space to the device 302. In such an embodiment, the user 350 may enter the menu by pressing a keyboard shortcut, or by gesturing within the field of the image sensor 314.

In some embodiments, the processor is configured to reverse engineer ergonomic quality metrics from device 302 usage orientations that the user 350 has categorized by ergonomic quality. For example, in such an embodiment, the user 350 may rank a usage orientation's ergonomic quality on a scale from one to ten, or one to one-hundred, for example based on whether the rated device 302 usage orientation is comfortable to him or her. In such an embodiment, a user 350 may select a usage orientation and click a button to display a menu. The menu could present an "assign quality" choice to the user 350. When the user 350 selects an "assign quality" choice, he or she is presented with numbers or measures of quality from which to select. When the user 350 clicks on one of the choices (e.g., 7 of 10), the quality metric 7 is assigned to the device 302 usage orientation.

Based on the ergonomic quality that the user 350 assigns to each device 302 usage orientation, the processor may determine an ergonomic quality metric. For example, if the user 350 categorizes a set of device 302 usage orientations a low ergonomic quality, then the processor may determine and store an ergonomic quality metric that defines device 302 usage orientations similar to the poorly-rated orientations as having a low ergonomic quality. In some embodiments, the processor may search for other similarities between device 302 usage orientations to create ergonomic quality metrics, for example: whether the pitch, yaw, and/or roll angles between the user 350's head with respect to the gravitational force exerted by the Earth falls within or outside of ranges of angles determined to be of poor ergonomic quality. The processor may use these similarities to determine new ergonomic quality metrics. Then the processor may use these ergonomic quality metrics to determine the ergonomic quality of new device 302 usage orientations.

After the processor determines the ergonomic quality, it can generate an ergonomic signal based at least in part on the determined ergonomic quality. For example, in one embodiment, if a user 350 has a satisfactory ergonomic quality (for example, one that is likely to minimize injury, strain, or fatigue), the processor may determine no ergonomic signal is necessary. In such an embodiment, when the user 350 receives a message with a medium ergonomic quality the processor may determine a gentle ergonomic signal that is configured to create a briefly visible message to the user 350 on his or her display and disappear from the display after a few seconds. In the same embodiment, when the user 350 receives a message with a poor ergonomic quality, the processor may generate a strong ergonomic signal that is configured to cause an audible tone to emanate from a speaker that continues until the user 350 changes his or her orientation.

In some embodiments, the processor may not output the ergonomic signal until the user 350 is interacting with image sensor 314. In such an embodiment, the processor may not output the ergonomic signal until the user 350 has used an input device, such as a key on a keyboard, to move an indicator on the graphical user 350 interface overtop of an icon representing the ergonomic measurement application.

Illustrative Methods for Ergonomic Measurement

Figure 4:
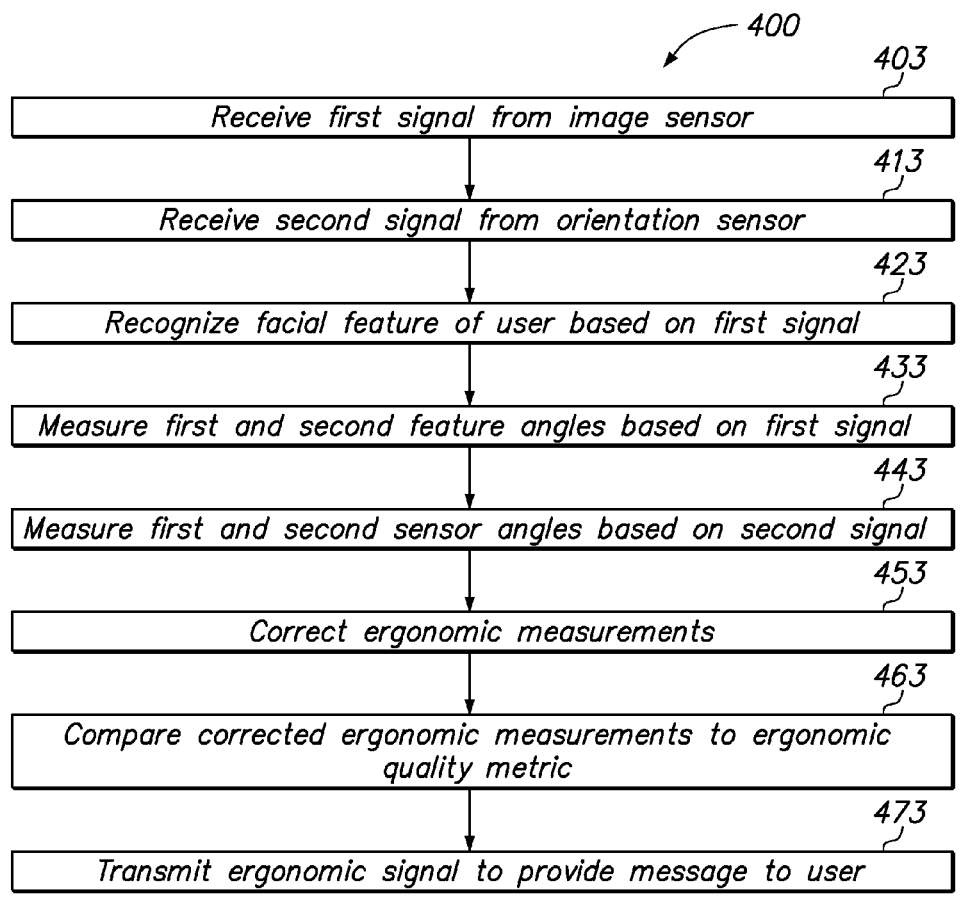
FIG. 4 is a flow chart for a method of ergonomic measurement according to one embodiment of the present invention.

FIG. 4 is a flow chart for a method of ergonomic measurement according to one embodiment of the present invention, which is discussed with respect to the system 100 shown in FIG. 1. The method 400 begins when processor 110 receives a first signal from the image sensor 114 comprising data as shown in box 403. The first signal comprises data associated with a user's orientation with respect to the image sensor 114, for example, an image of the user's head, neck, and shoulders appearing within the field of view of a charge-coupled device camera.

As shown in box 413, processor 110 receives a second signal from a orientation sensor 118, the second signal comprising data associated with the image sensor's 114 orientation with respect to gravity, the gravitational force exerted by the Earth. In one embodiment the orientation sensor 118 comprises, for example, a plurality of three MEMS accelerometers, each configured to measure acceleration along a different axis, for example the X-, Y-, and Z-axes. In other embodiments a different number of accelerometers may be used, or a different type of orientation sensor 118, such as a gyroscope or compass, may be used.

As shown in box 423, the method 400 further comprises recognizing a facial feature of the user based, at least in part, on the first signal received from the image sensor 114. For example, one or more of the several illustrative facial recognition techniques described above can be used to identify the location of the user's eyes, nose, and mouth. In other embodiments other portions of the user's body may be recognized, for example the user's shoulders, arms, and neck.

As shown in box 433, the method 400 further comprises measuring, based on data from the first signal from the image sensor 114, first and second feature angles between the recognized facial feature of the user and first and second axes associated with the orientation of the image sensor 114. For example, the first and second feature angles may comprise angles of pitch (whether the user's face is facing his feet or away from the rest of his body) and roll (whether the user's face is tilted toward his left shoulder or his right shoulder) between the user's recognized orientation and axes associated with the orientation of the image sensor 114. For example, one or more of the several illustrative facial recognition techniques described above can be used to identify the location of the user's eyes, nose, and mouth. In other embodiments fewer or greater numbers of measurements may be made. The axes associated with the orientation of the image sensor 114 may comprise a set of X-, Y-, and Z-axes with an origin at the image sensor 114, where the first axis runs along the display 116 of the device 102, and the second axis runs out into the field of view of the image sensor 114. In other embodiments, other coordinate measuring systems may be used; for example in one such embodiment a spherical coordinate system may be used to measure the orientation of one or more facial features of a user with respect to the image sensor 114.

As shown in box 443, the method 400 further comprises measuring, based on the data from the second signal from the orientation sensor 118, first and second sensor angles between the gravitational force exerted by the Earth and the first and second axes associated with the orientation of the image sensor 114, respectively, that were used to measure the first and second feature angles. For example, the first and second sensor angles may comprise angles of pitch and roll of the orientation of the image sensor 114 with respect to gravity using the same axes associated with the orientation of the image sensor 114 used to determine the angles of pitch and roll of the user with respect thereto. In another embodiment, a different set of coordinate axes, or type of coordinate axes, may be used to measure the orientation of the image sensor 114 with respect to gravity.

As shown in box 453, the method 400 further comprises correcting the ergonomic measurements. For example, in one embodiment the correction of the ergonomic measurement can comprise subtracting the first sensor angle from the first feature angle and subtracting the second sensor angle from the second feature angle. Such correction can provide, for example, a measure of the user's face's angles of pitch and roll with respect to the gravitational force exerted by the Earth, regardless of the current position or angle of the device he or she is using.

As shown in box 463, the method 400 further comprises comparing the corrected ergonomic measurements, such as corrected angles of pitch and roll of the user's face with respect to gravity, with an ergonomic quality metric, which can be, for example recognized guidelines for worker occupational health and safety. For example, ISO 9241-5, Ergonomic Requirements for Office Work with Visual Display Terminals (VDTs)—Part 5: Workstation Layout and Postural Requirements provides acceptable limits for a user's head orientation.

As shown in box 473, the method 400 further comprises transmitting an ergonomic signal to an output to provide a message to the user. For example, in one embodiment the processor 110 may send signals to both the speaker 120 and the display 116 to alert the user to his or her non-compliance with standards of good ergonomic positioning. In one such embodiment, the signal may be configured to give an audible warning tone to the user along with a pop-up window message indicating that he or she should sit up, refrain from slouching, take a break, or other action to correct his or her ergonomics. In one embodiment the system 100 may perform a measurement and provide an output message to the user upon a prompt from the user that he or she would like his or her ergonomics evaluated. In other embodiment the system 100 may be activated at all times when the device is powered on. In yet other embodiments the system 100 may make ergonomic measurements at regular periodic intervals as specified by the user or based on a default time period in the programming.

Figure 5:
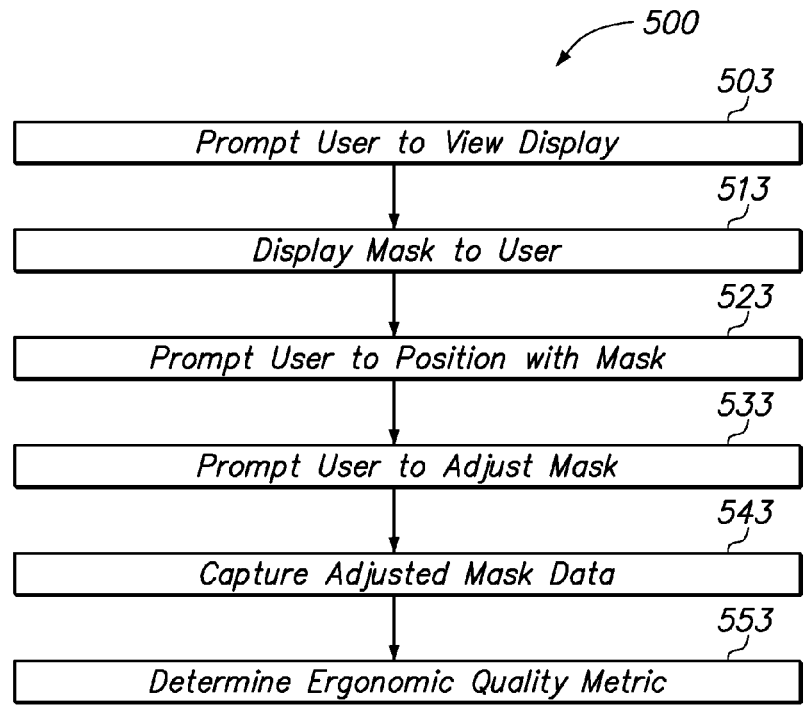
FIG. 5 is a flow chart for a method of ergonomic measurement according to one embodiment of the present invention.

Other methods according to embodiments of the present invention can be used to detect the orientation of a device user or to calibrate a system used to measure a user's ergonomic orientation, for example, to collect information about one or more acceptable orientations of a user's head, neck, shoulders, or other posture-related information using an image sensor. One embodiment that can be used to calibrate such a system, illustrated in the flow chart of FIG. 5 as method 500 that can be used to calibrate an ergonomic measurement system by determining a user-specific ergonomic quality metric.

As shown in box 503, a user is prompted to view a display device, such as a computer monitor or screen, from a comfortable position, such as seated on a chair, wherein the user's head and shoulders are within the field of view of an image sensor in communication with the same processor as the display device, such that the user is positioned at a distance from the display device within a predetermined range, for example the ergonomic standards ISO 9241-5 suggests the user should be positioned between 45 and 75 centimeters away from the display device.

As shown in box 513, the method 500 further includes displaying a mask in a user interface on the display device, such that the display is visible to the user. The mask can comprise, for example, an outlined shape resembling at least a portion of the user's body.

Next, as shown in box 523, the user is prompted to move at least a portion of his or her body within the field of view of the image sensor such that at least a portion of the user's body is visible on the display device in the same user interface as the outline of the mask on the display.

As shown in box 533, the user is prompted to adjust at least a portion of the mask to increase or decrease in size in one or more directions in order to closely align with the portion of the user's body visible in the data stream transmitted by the image sensor. In one embodiment the user may be prompted to adjust the size of the mask using an input device, such as a keyboard or mouse. For example, the user may be prompted to adjust the size of the head, neck, or shoulder-shaped portion of the mask to more closely align with his or her image in the user interface on the display as captured by the image sensor.

In another embodiment, the size or shape of the mask may be automatically adjusted to follow the contours of the outline of the user based on data received from the image sensor. For example, data associated with the contrast between a background object, such as a screen, and the user may be used to assist with recognition of the outline of at least a portion of the user, and the mask may be automatically adjusted to closely follow the user's outline.

As shown in box 543, the method 500 further comprises capturing data about the adjusted mask size comprising data associated with the user's orientation with respect to the image sensor once the mask has been adjusted to align with the user. Such data can be used to calibrate the system for that user's unique body size and/or shape.

As shown in box 553, the method 500 further comprises determining an ergonomic quality metric based at least in part on the adjusted mask data. The ergonomic quality metric can later be used by a processor when later determining an ergonomic measurement of the user. This box can comprise, for example, determining parameters for the user such as the shape and location of his or her head, neck, and shoulders, which can be used as calibration values in an ergonomic quality metric.

Figure 6:
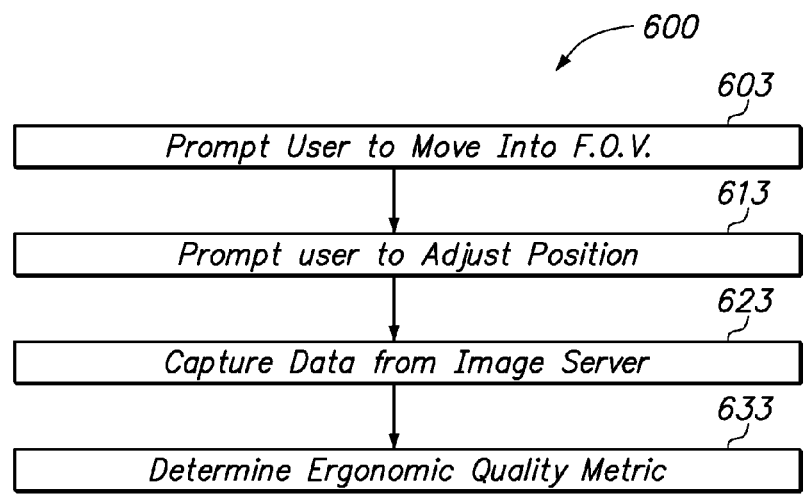
FIG. 6 is a flow chart for a method of ergonomic measurement according to one embodiment of the present invention.

In another embodiment that may be used to calibrate an ergonomic measurement system, illustrated in the flow chart of FIG. 6 as method 600, a user is prompted to display a predetermined pattern or object within the field of view of an image sensor, as shown in box 603. For example, the user may be prompted to attach one or more predetermined objects or patterns at specific locations on his or her body or clothing such that the objects or patterns are recognizable by the image sensor. In one embodiment, the objects can comprise circular discs of one or more different predetermined colors that are configured to be temporarily affixed to the user's shoulders to help ascertain the user's shoulder width.

As shown in box 613, the user may then be prompted to adjust at least a portion of his or her body's orientation with respect to the image sensor such that the predetermined objects or patterns are a known distance and/or angle from the image sensor.

As shown in box 623, method 600 further comprises capturing data from a signal provided by the image sensor comprising data associated with the user's orientation with respect to the to image sensor based at least in part on recognition of the predetermined objects or patterns attached to the user.

As shown in box 633, the captured data from the image sensor is used to determine an ergonomic quality metric for that user, which can be used to calibrate the system for that user's unique body size and/or shape. Using the example of objects affixed to each of the user's shoulders, the captured data can be used to measure the width of the user's shoulders at an acceptable distance from the display, thus providing an ergonomic quality metric for that user's shoulders. If the user moves closer to or farther away from the display, the distance between the user's shoulders will vary, and the system may be programmed to use the ergonomic quality metric associated with the calibration data for that user's shoulder width to determine whether the user has moved or adjusted his or her position such that it is too close or far from the display and may be likely to cause injury, strain, or fatigue.

Advantages of Systems for Ergonomic Measurement

Systems of ergonomic measurement provide users with many advantages. For example, embodiments of ergonomic measurement give users the ability to determine whether one or more aspects of their posture or how they are holding a device may tend to cause injury or muscle strain. This embodiment may be particularly useful for a user that spends long periods of time using a device in the same position, for example, while seated. Other embodiments of ergonomic measurement allow users to determine important information about their posture at repeated intervals throughout the course of a work period.

General Considerations

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

Embodiments in accordance with aspects of the present subject matter can be implemented in digital electronic circuitry, in computer hardware, firmware, software, or in combinations of the preceding. In one embodiment, a computer may comprise a processor or processors. The processor comprises or has access to a computer-readable medium, such as a random access memory (RAM) coupled to the processor. The processor executes computer-executable program instructions stored in memory, such as executing one or more computer programs including those configured to determine ergonomic measurements based on signals from image sensors and orientation sensors and stored ergonomic quality metric data, and suitable programming to produce ergonomic signals and to output the selected messages to the user as noted above.

Such processors may comprise, or may be in communication with, media, for example tangible computer-readable media, that may store instructions that, when executed by the processor, can cause the processor to perform the steps described herein as carried out, or assisted, by a processor.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations and/or additions to the present subject matter as would be readily apparent to one of ordinary skill in the art.

That which is claimed is:

1. A system comprising:
an image sensor configured to transmit a first signal comprising data associated with a user's orientation with respect to the image sensor;
an orientation sensor configured to transmit a second signal comprising data associated with the image sensor's orientation with respect to gravity;
a processor in communication with the image sensor and the orientation sensor, the processor configured to:
determine an ergonomic measurement of the user based at least in part on the first and second signals; and
transmit an ergonomic signal based at least in part on the ergonomic measurement;
recognize a facial feature of the user based at least in part on the first signal;
measure a first feature angle between the facial feature of the user and a first axis associated with the orientation of the image sensor based at least in part on the first signal;
measure a first sensor angle between the first axis associated with the orientation of the image sensor and gravity based at least in part on the second signal;
correct at least a first portion of the ergonomic measurement by subtracting the first sensor angle from the first feature angle; and
an output in communication with the processor and configured to provide a message to the user based at least in part on the ergonomic signal.

2. The system of claim 1, wherein: the processor is further configured to receive a third signal comprising an ergonomic quality metric; and the ergonomic signal is based at least in part on the third signal.

3. The system of claim 2, wherein the ergonomic quality metric is based at least in part on an ergonomic guideline.

4. The system of claim 2, wherein the ergonomic quality metric comprises a user-defined value.

5. The system of claim 2, wherein the ergonomic quality metric comprises a default value.

6. The system of claim 1, wherein the orientation sensor comprises an accelerometer.

7. The system of claim 1, wherein the orientation sensor comprises a gyroscope.

8. The system of claim 1, wherein the output comprises a display.

9. The system of claim 1, further comprising a display in communication with the processor, and wherein the processor is further configured to transmit display signals to the display.

10. The system of claim 1, further comprising a housing, and wherein the orientation sensor and the processor are mounted inside the housing.

11. The system of claim 10, wherein the housing is a mobile device housing.

12. The system of claim 10, wherein the housing is a mobile computing device housing.

13. A method comprising:
receiving a first signal from an image sensor, the first signal comprising data associated with a user's orientation with respect to the image sensor;
receiving a second signal from an orientation sensor, the second signal comprising data associated with the image sensor's orientation with respect to gravity;
determining an ergonomic measurement of the user based at least in part on the first and second signals;
recognizing a facial feature of the user based at least in part on the first signal;
measuring a first feature angle between the facial feature of the user and a first axis associated with the orientation of the image sensor based at least in part on the first signal;
measuring a first sensor angle between the first axis associated with the orientation of the image sensor and gravity based at least in part on the second signal;
correcting at least a first portion of the ergonomic measurement by subtracting the first sensor angle from the first feature angle.

14. The method of claim 13, further comprising: transmitting an ergonomic signal based at least in part on the ergonomic measurement to an output configured to provide a message to the user.

15. The method of claim 13, wherein determining the ergonomic measurement of the user further comprises:

measuring a second feature angle between the facial feature of the user and a second axis associated with the orientation of the image sensor based at least in part on the first signal;

measuring a second sensor angle between the second axis associated with the orientation of the image sensor and gravity based at least in part on the second signal;

correcting at least a second portion of the ergonomic measurement by subtracting the second sensor angle from the second feature angle.

16. The method of claim 13, wherein the ergonomic measurement of the user is determined, at least in part, on an ergonomic quality metric.

17. The method of claim 13, wherein the ergonomic measurement of the user is determined at predetermined intervals.

18. The method of claim 13, wherein the ergonomic measurement of the user is determined based at least in part on a user input command.

19. A non-transitory computer readable medium comprising program code configured to:

receive a first signal from an image sensor, the first signal comprising data associated with a user's orientation with respect to the image sensor;

receive a second signal from an orientation sensor, the second signal comprising data associated with the image sensor's orientation with respect to gravity;

determine an ergonomic measurement of the user based at least in part on the first and second signals;

recognize a facial feature of the user based at least in part on the first signal;

measure a first feature angle between the facial feature of the user and a first axis associated with the orientation of the image sensor based at least in part on the first signal;

measure a first sensor angle between the first axis associated with the orientation of the image sensor and gravity based at least in part on the second signal;

correct at least a first portion of the ergonomic measurement by subtracting the first sensor angle from the first feature angle.

20. The non-transitory computer readable medium of claim 19, further comprising program code configured to: transmit an ergonomic signal based at least in part on the ergonomic measurement to an output configured to provide a message to the user.

21. The non-transitory computer readable medium of claim 20, further comprising program code configured to:

measure a second feature angle between the facial feature of the user and a second axis associated with the orientation of the image sensor based at least in part on the first signal;

measure a second sensor angle between the second axis associated with the orientation of the image sensor and gravity based at least in part on the second signal;

correct at least a second portion of the ergonomic measurement by subtracting the second sensor angle from the second feature angle.

22. The system of claim 1, wherein the processor is further configured to:

measure a second feature angle between the facial feature of the user and a second axis associated with the orientation of the image sensor based at least in part on the first signal;

measure a second sensor angle between the second axis associated with the orientation of the image sensor and gravity based at least in part on the second signal;

correct at least a second portion of the ergonomic measurement by subtracting the second sensor angle from the second feature angle.

* * * * *